US012142352B2

(12) United States Patent
Bashir et al.

(10) Patent No.: US 12,142,352 B2
(45) Date of Patent: Nov. 12, 2024

(54) MODULAR PATIENT ANALYTICS

(71) Applicant: KONINKLIJKE PHILIPS N.V., Eindhoven (NL)

(72) Inventors: Bilal Bashir, Methuen, MA (US); Trevor Merrill, Londonderry, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 326 days.

(21) Appl. No.: 16/592,834

(22) Filed: Oct. 4, 2019

(65) Prior Publication Data
US 2020/0168305 A1 May 28, 2020

Related U.S. Application Data

(60) Provisional application No. 62/749,706, filed on Oct. 24, 2018.

(51) Int. Cl.
| | |
|---|---|
| *G16H 10/60* | (2018.01) |
| *G06F 3/0482* | (2013.01) |
| *G06F 3/04847* | (2022.01) |
| *G06N 20/00* | (2019.01) |

(52) U.S. Cl.
CPC ............ *G16H 10/60* (2018.01); *G06N 20/00* (2019.01); *G06F 3/0482* (2013.01); *G06F 3/04847* (2013.01)

(58) Field of Classification Search
CPC ........ G16H 10/00; G16H 10/60; G06N 20/00; G06F 3/0482; G06F 3/04847

USPC ....................................................... 705/3, 703
See application file for complete search history.

(56) References Cited

U.S. PATENT DOCUMENTS

| | | | |
|---|---|---|---|
| 7,024,370 B2 | 4/2006 | Epler et al. | |
| 10,453,165 B1* | 10/2019 | Kostov | .................. G06N 20/00 |
| 2011/0178717 A1* | 7/2011 | Goodnow | .............. G16H 15/00 |
| | | | 702/19 |
| 2013/0158968 A1* | 6/2013 | Ash | ........................ G16H 50/20 |
| | | | 703/11 |
| 2014/0095201 A1 | 4/2014 | Farooq et al. | |

(Continued)

OTHER PUBLICATIONS

Case Study. "Using Machine Learning and EMR Data to Predict Patient Decline." Intel. 2017.

(Continued)

*Primary Examiner* — Hwei-Min Lu

(57) ABSTRACT

A modular patient analytics system, including: an integrated machine learning module configured to receive patient data and to apply machine learning models to the received patient data; machine learning services that includes default machine learning models and trained machine learning models; a testing service configured to receive real time patient data, to run a machine learning model to produce a model output, and to provide the model output to the integrated machine learning module; a model training service configured to receive site training data, to train a machine learning model using the site training data, and to provide the trained machine learning model to the machine learning services; and a classification service configured to receive and provide pseudo labels for patient data from the (Continued)

site data for use in semi supervised learning of machine learning models as well as model validation on updated and existing machine learning models.

25 Claims, 7 Drawing Sheets

(56) References Cited

U.S. PATENT DOCUMENTS

| | | | | |
|---|---|---|---|---|
| 2015/0112710 | A1* | 4/2015 | Haber | G16H 50/50 |
| | | | | 705/2 |
| 2015/0193583 | A1* | 7/2015 | McNair | G16H 50/20 |
| | | | | 705/2 |
| 2015/0269337 | A1* | 9/2015 | Schulte | G16Z 99/00 |
| | | | | 705/3 |
| 2015/0324527 | A1* | 11/2015 | Siegel | G16B 50/30 |
| | | | | 705/3 |
| 2015/0339442 | A1 | 11/2015 | Oleynik | |
| 2015/0379429 | A1* | 12/2015 | Lee | G09B 5/00 |
| | | | | 706/11 |
| 2016/0166209 | A1* | 6/2016 | Itu | A61B 6/5217 |
| | | | | 600/408 |
| 2017/0032243 | A1 | 2/2017 | Corrado et al. | |
| 2017/0061093 | A1* | 3/2017 | Amarasingham | G16H 10/60 |
| 2017/0277841 | A1* | 9/2017 | Shankar | G16Z 99/00 |
| 2018/0053123 | A1* | 2/2018 | Sorkey | G16H 10/60 |
| 2019/0012559 | A1* | 1/2019 | Desappan | G06V 10/764 |
| 2019/0106732 | A1* | 4/2019 | Spurlock, III | C12Q 1/6883 |
| 2019/0108417 | A1* | 4/2019 | Talagala | G06N 20/00 |
| 2020/0105376 | A1* | 4/2020 | Lai | G16B 50/30 |

OTHER PUBLICATIONS

Badgeley MA, et al., BMJ Open "EHDViz: clinical dashboard development using open-source technologies." 2016;6: e010579. doi:10.1136/bmjopen-2015-010579.

Dasta, J.F. et al., "Daily cost of an intensive care unit day: the contribution of mechanical ventilation." (Jun. 2005). Retrieved from Pubmed: https://www.ncbi.nlm.nih.gov/pubmed/15942342.

Gordon, R. (Aug. 21, 2017). Retrieved from MIT News: http://news.mit.edu/2017/using-machine-learning-improve-patient-care-0821.

Taheri, P.A. et al., "Length of stay has minimal impact on the cost of hospital admission." (Aug. 2000). Retrieved from PubMed: https://www.ncbi.nlm.nih.gov/pubmed/10945354.

Churpek, M.M. et al. Using Electronic Health Record Data to Develop and Validate a Prediction Model for Adverse Outcomes on the Wards. (Apr. 1, 2015). Retrieved from PMC: https://www.ncbi.nlm.nih.gov/pmc/articles/PMC3959228/.

* cited by examiner

Concept catalog

Search for: Arterial blood pressure ⌄ — 324

Search type: Anywhere in the string ⌄ — 326

Results: ☐ Search within results

| Concepts and terms | Parent concept |
|---|---|
| Arterial blood pressure | Arterial blood press... |
| Arterial blood pressure | Arterial blood press... |
| Arterial blood pressure | Arterial blood press... |
| Arterial blood pressure (observable entity) | Blood pressure (ob... |
| Arterial blood pressure (observable entity) | Arterial measure (o... |
| Arterial blood pressure (observable entity) | Vascular meaure ( ... |
| Arterial blood pressure catheter | Arterial blood press... |
| Arterial blood pressure catheter | Arterial blood press... |
| Arterial blood pressure catheter | Arterial blood press... |
| Arterial blood pressure (physical ... | Hemodynamic mea... |
| Arterial blood pressure (physical ... | Monitor, device (ph... |
| Arterial blood pressure (physical ... | Catheter, device (p... |
| Non-invasive arterial blood pressure monit... | Arterial pressure m... |
| Taking arterial blood pressure | Taking arterial bloo... |
| Taking arterial blood pressure (procedure) | Blood pressure taki... |

— 328

SNOMED CT concepts — 322

- Cardiovascular function (observable entity)
  - Auscultatory gap (observable entry)
  - ⊞ Blood erythrocyte concentration (observable entity)
  - ⊞ Blood erythrocyte volume (observable entity)
  - Blood fluidity (observable entity)
  - ⊞ Blood oxygen pressure (observable entity)
  - Blood plasma volume (observable entity)
  - Blood pressure (observable entity)
    - ⊞ 24 hour blood pressure (observable entry)
    - Ankle brachial pressure index (observable entity)
    - ⊞ Arterial blood pressure (observable entity)
    - ⊞ Arterial pulse pressure (observable entity)
    - ⊞ Arterial wedge pressure (observable entity)
    - ⊞ Average blood pressure (observable entity)
    - ⊞ Diastolic blood pressure (observable entity)
    - Dorsalis pedis arterial pressure (observable entity)
    - ⊞ Intercardiac pressure (observable entity)
    - ⊞ Invasive blood pressure (observable entity)

— 330

Concept details

- Arterial blood pressure (observable entity)
- ⊟ SNOMED ID
  - 386534000
- ⊟ Terms
  - Arterial blood pressure (observable entity)
  - Arterial blood pressure
- ⊟ Super concepts
  - Blood pressure (observable entity)
  - Arterial measure (observable entity)
  - Vascular measure (observable entity)

— 332

[ OK ]  [ Cancel ]

FIG. 3

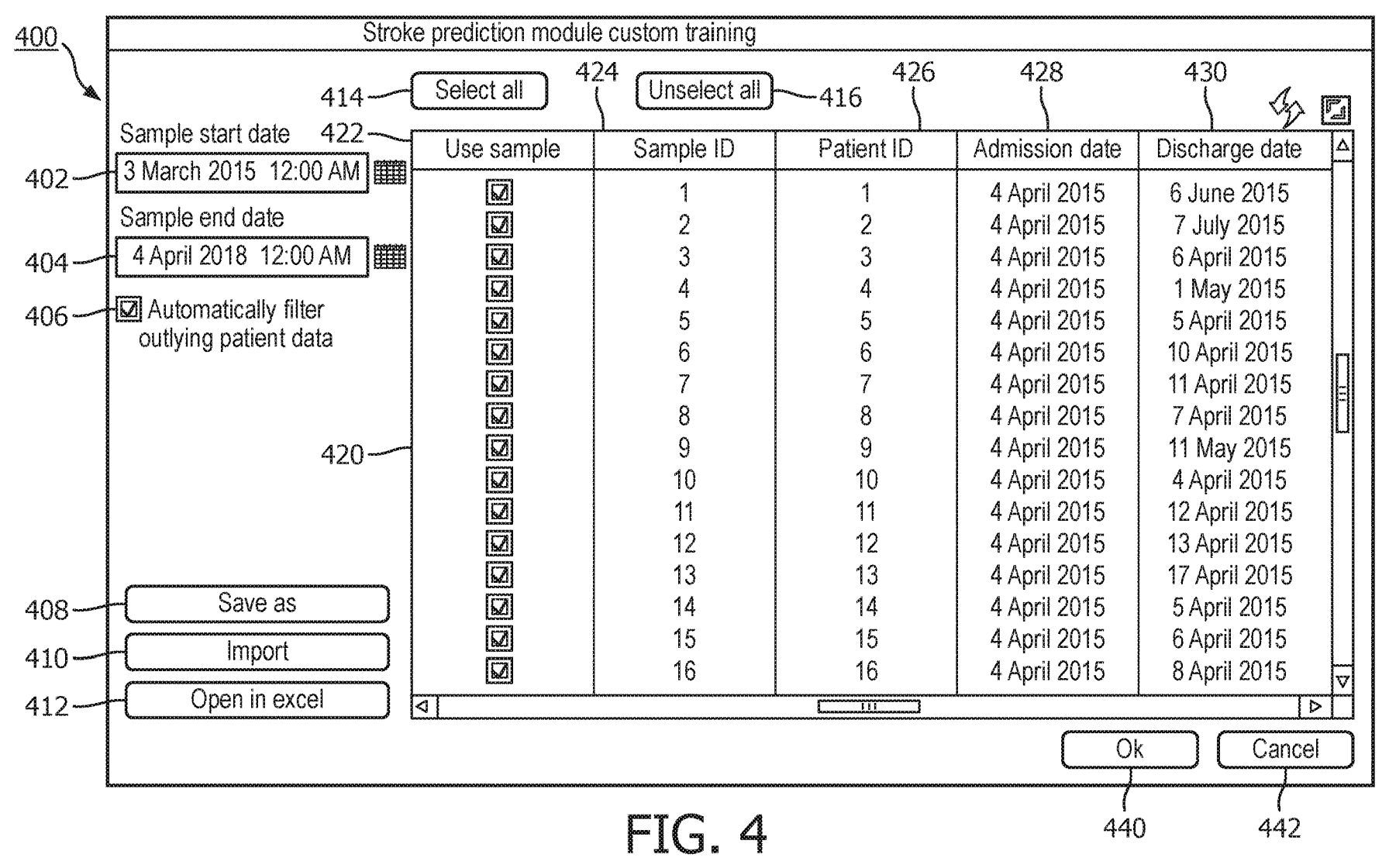

Stroke prediction module custom training — 414

- 402 Sample start date: 3 March 2015 12:00 AM — 422
- 404 Sample end date: 4 April 2018 12:00 AM
- 406 ☑ Automatically filter outlying patient data 424 Select all    416 Unselect all

| Use sample | Sample ID | Patient ID | Admission date | Discharge date |
|---|---|---|---|---|
| ☑ | 1 | 1 | 4 April 2015 | 6 June 2015 |
| ☑ | 2 | 2 | 4 April 2015 | 7 July 2015 |
| ☑ | 3 | 3 | 4 April 2015 | 6 April 2015 |
| ☑ | 4 | 4 | 4 April 2015 | 1 May 2015 |
| ☑ | 5 | 5 | 4 April 2015 | 5 April 2015 |
| ☑ | 6 | 6 | 4 April 2015 | 10 April 2015 |
| ☑ | 7 | 7 | 4 April 2015 | 11 April 2015 |
| ☑ | 8 | 8 | 4 April 2015 | 7 April 2015 |
| ☑ | 9 | 9 | 4 April 2015 | 11 May 2015 |
| ☑ | 10 | 10 | 4 April 2015 | 4 April 2015 |
| ☑ | 11 | 11 | 4 April 2015 | 12 April 2015 |
| ☑ | 12 | 12 | 4 April 2015 | 13 April 2015 |
| ☑ | 13 | 13 | 4 April 2015 | 17 April 2015 |
| ☑ | 14 | 14 | 4 April 2015 | 5 April 2015 |
| ☑ | 15 | 15 | 4 April 2015 | 6 April 2015 |
| ☑ | 16 | 16 | 4 April 2015 | 8 April 2015 |

- 408 Save as
- 410 Import
- 412 Open in excel
- 440 Ok
- 442 Cancel

FIG. 4

MODULAR PATIENT ANALYTICS

CROSS-REFERENCE TO PRIOR APPLICATIONS

This patent application claims the priority benefit under 35 U.S.C. § 119(e) of U.S. Provisional Application No. 62/749,706, filed on Oct. 24, 2018, the contents of which are herein incorporated by reference.

TECHNICAL FIELD

Various exemplary embodiments disclosed herein relate generally to modular patient analytics.

BACKGROUND

Clinicians are often inundated by test results, charts and other data for multiple patients when making real time treatment decisions. As a result, because of this data overload, sometimes it is difficult for clinicians to recognize the important information indicating health issues in their patients. Also, clinicians are not always motivated to chart information on their patients, because such data adds to the data overload and it is not always clear that any given information may be important in treatment decisions.

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a modular patient analytics system, including: an integrated machine learning module configured to receive patient data from site data and to apply machine learning models to the received patient data; machine learning services that includes default machine learning models and trained machine learning models; a testing service configured to receive real time patient data, to run a machine learning model from the machine learning services to produce a model output, and to provide the model output to the integrated machine learning module; and a model training service configured to receive site training data, to train a first machine learning model using the site training data, and to provide the trained first machine learning model to the machine learning services.

Various embodiments are described, further including a patient data graphical user interface configured to extract patient data from the site data to provide received patient data to the integrated machine learning module.

Various embodiments are described, further including a patient analytics modules graphical user interface configured to allow a user to select which machine learning models to use from the machine learning services.

Various embodiments are described, wherein the patient data graphical user interface presents a list of machine learning modules based upon the types of patient data available in the site data.

Various embodiments are described, wherein the patient data graphical user interface is configured to receive an input from the user to validate a selected machine learning module.

Various embodiments are described, wherein the patient data graphical user interface is configured to receive an input from the user to unregister a selected machine learning module.

Various embodiments are described, wherein the patient data graphical user interface is configured to receive an input from the user to update a selected machine learning module.

Various embodiments are described, wherein the patient data graphical user interface is configured to display validation information regarding the selected machine learning module.

Various embodiments are described, wherein the validation information includes at least one of validation status, validation date, local validation accuracy, and generic database accuracy.

Various embodiments are described, further including an overall risk graphical user interface configured to display patient risk information for a selected patient based upon applying machine learning models in the integrated machine learning module to patient data of the selected patient.

Various embodiments are described, wherein the overall risk graphical user interface further includes a listing of patient risks, an associated risk level, and associated leading contributors.

Various embodiments are described, wherein the overall risk graphical user interface further includes set of icons indicating various body systems of the patient wherein the appearance of the icon is varied based upon the risk level for each body system of the selected patient.

Various embodiments are described, wherein the overall risk graphical user interface further includes an overall risk assessment of the patient.

Various embodiments are described, wherein the overall risk graphical user interface further includes set of icons indicating patient care alerts.

Various embodiments are described, wherein the patient care alerts include one of nutrition, fluids, waste, activity, and medication.

Various embodiments are described, further including a machine learning model registration configuration graphical user interface configured to display machine learning model inputs and associated internal mappings, encodings, normalization minimums, and normalization maximums.

Various embodiments are described, wherein the machine learning model registration configuration graphical user interface is configured to allow a user to change the values for the associated internal mappings, normalization minimums, and normalization maximums.

Various embodiments are described, further including a module custom training graphical user interface configured to allow a user to display sample patient data and to select site training data to train the first machine learning model.

Various embodiments are described, wherein the module custom training graphical user interface is configured to allow a user to select a start date and end date for the sample patient data and to select sample patient data based upon the selected start date and end date.

Various embodiments are described, wherein the module custom training graphical user interface includes a save as icon and an import icon, wherein the selected sample patient data is saved when the user selects the save as icon and sample patient data is imported from an external source when the user selects the import icon.

Various embodiments are described, further including a classification service configured to receive patient data from the site data and run a first machine learning model on the received patient data to validate the second machine learning model.

Various embodiments are described, further including a classification service configured to receive vetted data and run the machine learning model on the received vetted data to validate the first machine learning model.

Further various embodiments relate to a method, including: receiving, by an integrated machine learning module, patient data from site data and to applying machine learning models to the received patient data; providing, by machine learning services, default machine learning models and trained machine learning models; receiving, by a testing service, real time patient data, to run a machine learning model from the machine learning services to produce a model output, and to provide the model output to the integrated machine learning module; and receiving, by a model training service, site training data to train a first machine learning model using the site training data and to provide the trained first machine learning model to the machine learning services.

Various embodiments are described, further including extracting, by a patient data graphical user interface, patient data from the site data to provide received patient data to the integrated machine learning module.

Various embodiments are described, further including allowing, by a patient analytics modules graphical user interface, a user to select which machine learning models to use from the machine learning services.

Various embodiments are described, wherein the patient data graphical user interface presents a list of machine learning modules based upon the types of patient data available in the site data.

Various embodiments are described, further including receiving, by the patient data graphical user interface, an input from the user to validate a selected machine learning module.

Various embodiments are described, further including receiving, by the patient data graphical user interface, an input from the user to unregister a selected machine learning module.

Various embodiments are described, further including receiving, by the patient data graphical user interface, an input from the user to update a selected machine learning module.

Various embodiments are described, further including displaying, by the patient data graphical user interface, validation information regarding the selected machine learning module.

Various embodiments are described, wherein the validation information includes at least one of validation status, validation date, local validation accuracy, and generic database accuracy.

Various embodiments are described, further including displaying, by an overall risk graphical user interface, patient risk information for a selected patient based upon applying machine learning models in the integrated machine learning module to patient data of the selected patient.

Various embodiments are described, wherein the overall risk graphical user interface further includes a listing of patient risks, an associated risk level, and associated leading contributors.

Various embodiments are described, wherein the overall risk graphical user interface further includes set of icons indicating various body systems of the patient wherein the appearance of the icon is varied based upon the risk level for each body system of the selected patient.

Various embodiments are described, wherein the overall risk graphical user interface further includes an overall risk assessment of the patient.

Various embodiments are described, wherein the overall risk graphical user interface further includes set of icons indicating patient care alerts.

Various embodiments are described, wherein the patient care alerts include one of nutrition, fluids, waste, activity, and medication.

Various embodiments are described, further including displaying, by a machine learning model registration configuration graphical user interface, machine learning model inputs and associated internal mappings, encodings, normalization minimums, and normalization maximums.

Various embodiments are described, wherein the machine learning model registration configuration graphical user interface is configured to allow a user to change the values for the associated internal mappings, normalization minimums, and normalization maximums.

Various embodiments are described, further including allowing, by a module custom training graphical user interface, a user to display sample patient data and to select site training data to train the first machine learning model.

Various embodiments are described, wherein the module custom training graphical user interface is configured to allow a user to select a start date and end date for the sample patient data and to select sample patient data based upon the selected start date and end date.

Various embodiments are described, wherein the module custom training graphical user interface includes a save as icon and an import icon, wherein the selected sample patient data is saved when the user selects the save as icon and sample patient data is imported from an external source when the user selects the import icon.

Various embodiments are described, further including receiving, by a classification service, patient data from the site data and running a first machine learning model on the received patient data to validate the second machine learning model.

Various embodiments are described, further including receiving, by a classification service, vetted data and running the machine learning model on the received vetted data to validate the first machine learning model.

BRIEF DESCRIPTION OF THE DRAWINGS

In order to better understand various exemplary embodiments, reference is made to the accompanying drawings, wherein:

FIG. 4 illustrates the custom training data GUI;

To facilitate understanding, identical reference numerals have been used to designate elements having substantially the same or similar structure and/or substantially the same or similar function.

DETAILED DESCRIPTION

Figure 1:
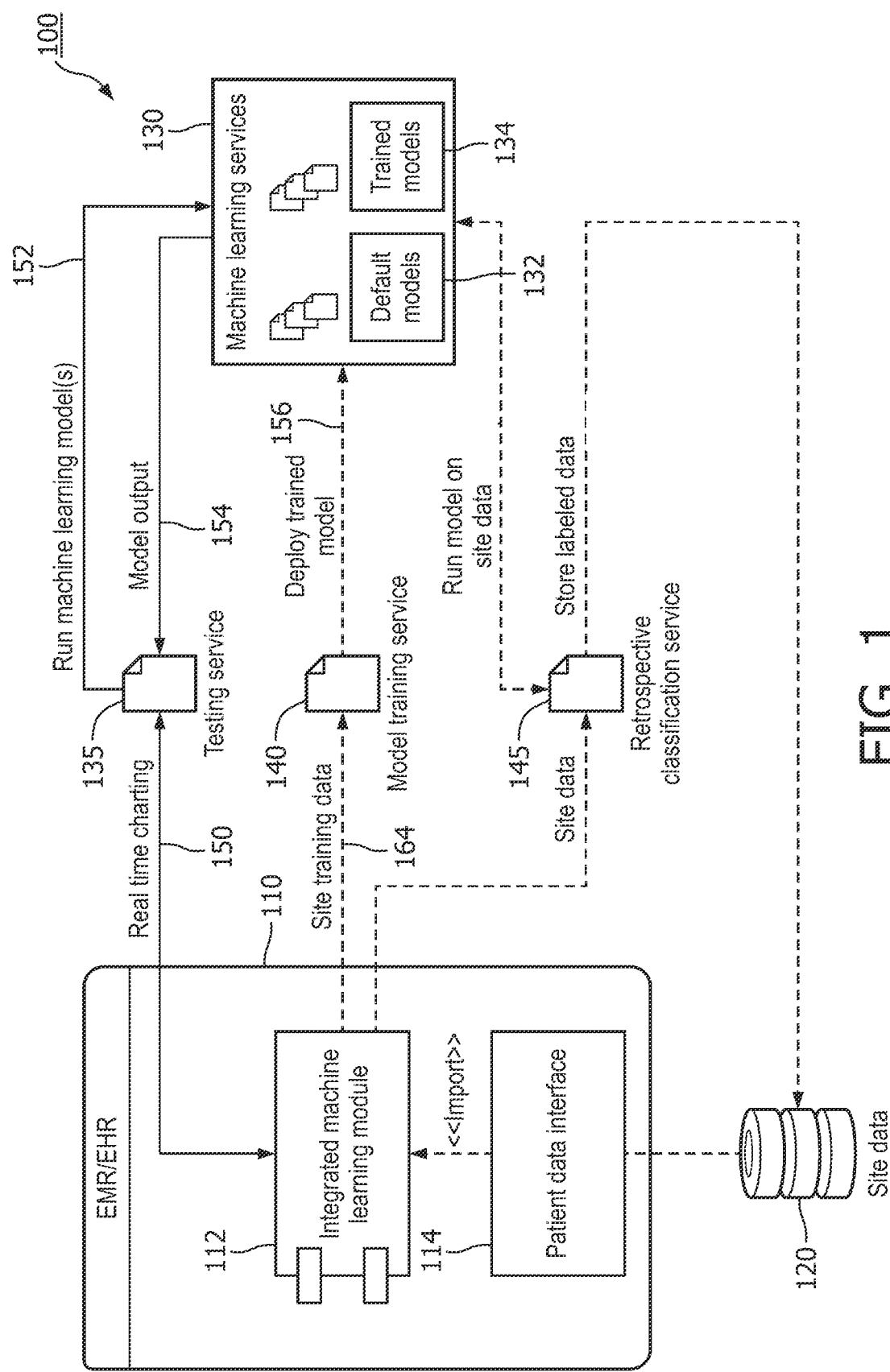
FIG. 1 illustrates the implementation of a modular patient analytics system integrated in an electronic medical records (EMR) system.

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

In order to use the large amount of data collected on patients, new and innovative ways to integrate machine learning and patient analytics into electronic medical records (EMR) products will be described. The modular patient analytics system described herein provides various technical advantages such as helping to prevent data overload of clinicians, extracting various information about patient conditions and health issues from the patient EMR data, and encouraging clinicians to chart medical data for patients without the fear of data overload and so that such data may be used to detected and predict patient medical conditions and issues. Further, the modular patient analytics system allows users to integrate new patient analytics modules as desired and as they become available into EMR systems. The patient analytics modules will allow for predictive analysis of high-risk and other desired conditions. The modular patient analytics system may be fully integrated with the EMR system in the form of an overview document or display with real time active alerts as well as the ability to partially integrate analytics into existing forms and workflows. The analytic modules may be qualified against existing external patient data. Alternately, clinicians will have the option to train patient analytics modules against their own clinical data and validate against vetted data. The modular patient analytics system will also allow clinicians to preemptively diagnose high risk conditions and manage patient care more efficiently, ever improving as patient predictive analytics evolves.

Clinicians are often inundated by test results, charts, and other data for multiple patients when making real time treatment decisions. Intelligent machine learning models integrated into modern EMR systems may alleviate this problem via testing patient data against models trained from previous outcomes to provide the most important signals for each patient's care and outcome. Simplifying data output for clinicians may also lead to increased usage and charting of patient data and product adoption of EMR systems by providing an incentive for users to chart more often and more complete data.

Current EMR systems do not allow for frequent product updates limiting the viability for an integrated machine learning solution. A module-based solution that interfaces with EMR systems allows for frequent updates with minimal down time. Machine learning models may be updated more frequently and do not need to be tied to the development cycles of EMR systems. Integrating a new analytical module would be no more disruptive to the end user than an update to the EMR configuration settings.

Current machine learning solutions exist to provide retrospective classification of patient data. The modular patient analytics system may run patient data against machine learning models as it is charted allowing for real time decision making, leading to earlier diagnosis and efficient patient care. Prior studies have found a reduction in length of stay for survivors admitted to ICUs by as much as 1 full day reduces the total cost of care on average by 3%, which still represents significant cost savings that can be achieved. Aside from providing early warning signs for serious patient conditions such as sepsis, heart disease, etc., patient care may also be improved by providing clinicians with strong predictors for the patients' needs. For example, given a patient's vital signs, machine learning models may provide real time information on whether the patient should be fed or needs physical activity or if a dangerous condition is arising.

Limited accuracy and scope of machine learning models can lead to missed opportunities and inefficient resource utilization. Research has shown that using EMR data of institutions results in improved prediction models compared to models based on more generic patient data. Similarly, research on EHR model transfer methods, shows that site specific clinical data improves accuracy of predictive models for mortality and length of stay. The modular patient analytics systems described herein overcomes the limited accuracy problem by integrating directly into EMR systems, allowing models to be trained on site specific patient data for more accurate results than currently available.

The modular patient analytics system relies on standardized coding systems, such as for example, systematized nomenclature of medicine (SNOMED) or logical observation identifiers names and codes (LOINC), for features used by the analytics model for classification, enabling integration with any product that utilizes coding systems for patient data. Using coding systems overcomes the need for burdensome interfacing of data while also making the modular patient analytics system viable as a standalone product. This flexibility shortens the time to implementation in the field from approval and integration of new analytical algorithms into current EMR systems without being tied to the development or upgrade cycle of the EMR systems.

Currently patient care relies heavily on clinician experience and hospital operating procedures. Integration of the modular patient analytics system into existing EMR systems familiarizes clinicians with the latest and approved medical analytical methods. As well as providing a platform for greater collaboration between hospital departments and patient facing clinicians for purposes of resource management and identifications of inefficiencies.

FIG. 1 illustrates the implementation of a modular patient analytics system integrated in an EMR system. The modular patient analytics system 100 may include an EMR system 110, a testing service 135, a model training service 140, a retrospective classification service 145, a machine learning services 130, and site data 120. Each of these will now be described.

The site data 120 is data that has been collected by a medical site where the modular patient analytics system 100 has been deployed. The site data 120 will include all of the EMR data collected for patients. This EMR data will be historical data collected for the patient, which may include data collected for the patient form other medical facilities, as well as recently collected data and real time data collected for the patient.

The EMR system 110 collects, organizes, and stores patent data that is stored in the site data 120. The EMR system may provide a user interface to be used by a clinician to chart patient data. Further, the EMR system 110 may provide a user interface for a clinician that provides access to patient EMR data as well as to provide an overview document or display with real time active alerts, real time suggestions of patient actions, and patient status. The EMR system 110 will include the various functions and components typically included in such EMR systems. Additionally, the EMR system 110 may include integrated machine learning modules 112. These integrated machine learning modules 112 are designed to be modular in that they may be added and removed from the EMR system 110 as desired and needed by the clinician. Further, these integrated machine learning modules 112 may be updated with newer and better models as they become available. Also, these integrated machine learning modules 112 may be tailored by training them using local clinical data to provide the benefits described above. These integrated machine learning modules 112 are used by the EMR system 110 to evaluate patients using the patients EMR data, which evaluations are then presented to the clinician as alerts or actions to take for the patient. As patient data is collected by the EMR 110, this collected data is provided to the integrated machine learning modules 112 which can run the collected data through a testing service 135 enabling evaluations on data charted in real time 150.

The EMR system 110 may include a patient data interface 114 that extracts patient data from the site data 120 for use by the integrated machine learning modules 112. The patient data interface 114 determines the specific patient data needed for a given integrated machine learning module 112 and extracts that data from the site data 120. The patient data interface 114 may further format or preprocess the data as may be required by the integrated machine learning module 112 and provides the specific patient data to the integrated machine learning module 112. This data may be used for training machine learning models, model verification, etc. As will be further described below, the patient data may be coded using SNOMED or LOINC coding systems.

The machine learning services 130 provides various machine learning models that may be integrated into the EMR system 110 as integrated machine learning modules 112. The machine learning service 130 may include a wide variety of machine learning models that have been developed and verified to predict various medical conditions or to provide various medical advice regarding patient needs. For example, machine learning models may predict conditions such as stroke, heart attack, respiratory distress, etc. Also, machine learning models may predict when a patient should be fed, needs physical activity, etc. The clinician may then select which machine learning models to use to analyze patient data. Also, all machine learning models may not be available to a clinician based upon the data available in the site data 120. The machine learning services 130 (or alternatively the EMR system 110) may analyze the various data schemas used in the site data 120 to determine which machine learning models are available based upon the availability of the patient data required for the model. It is noted, that various machine learning models for predicting a specific condition may be available using different patient data. Such machine learning models may also have different levels of accuracy. In such a case, only the most accurate machine learning models may be provided or suggested. In other embodiments, all potential models may be provided, and the EMR system 110 may use the highest accuracy machine learning model available based upon the patient data available, as the data available for patients may vary from patient to patient.

The machine learning services 130 further includes default machine learning models 132. These default machine learning models are models that have been trained using external patient data. The machine learning services 130 further includes trained machine learning models 134 that take existing model templates and trains them using training data from the site data 120. This training may be carried out by the model training service 140. The model training service 140 may receive a request for training a machine learning model using site data 120. The request will identify the data needed to train the machine learning model. The model training service 140 will then obtain the needed site training data 164 from the site data 120 either directly or via the EMR system 110. The model training service 140 then may train the machine learning model using the site training data and then deploy the trained machine learning model 156 to the machine learning services 130, which then provides the model for use by the testing service 135 or retrospective classification service 145.

The retrospective classification services 145 allows for improved accuracy when training machine learning models and the validation of new and existing models integrated in machine learning services 130. The retrospective classification service 145 obtains site data form the integrated machine learning model 112 to provide labels for existing site data. The pseudo labeled site data can then be used to train a more accurate machine learning model as well as be used for machine learning model validation such as Resubstituting, Hold-out, K-fold cross-validation, LOOCV, Random subsampling and boot strapping.

The testing service 135, receives charted patient data in real time 150. This data is then used to run machine learning models 152 as selected by the user of the system. The models are from the machine learning services 130 and may be either default machine learning models 132 or trained machine learning models 134. The testing service 135 receives the model output 154. These model outputs may then be displayed and/or provided to a care provider. Examples, of such interfaces will be presented below.

Figure 2:
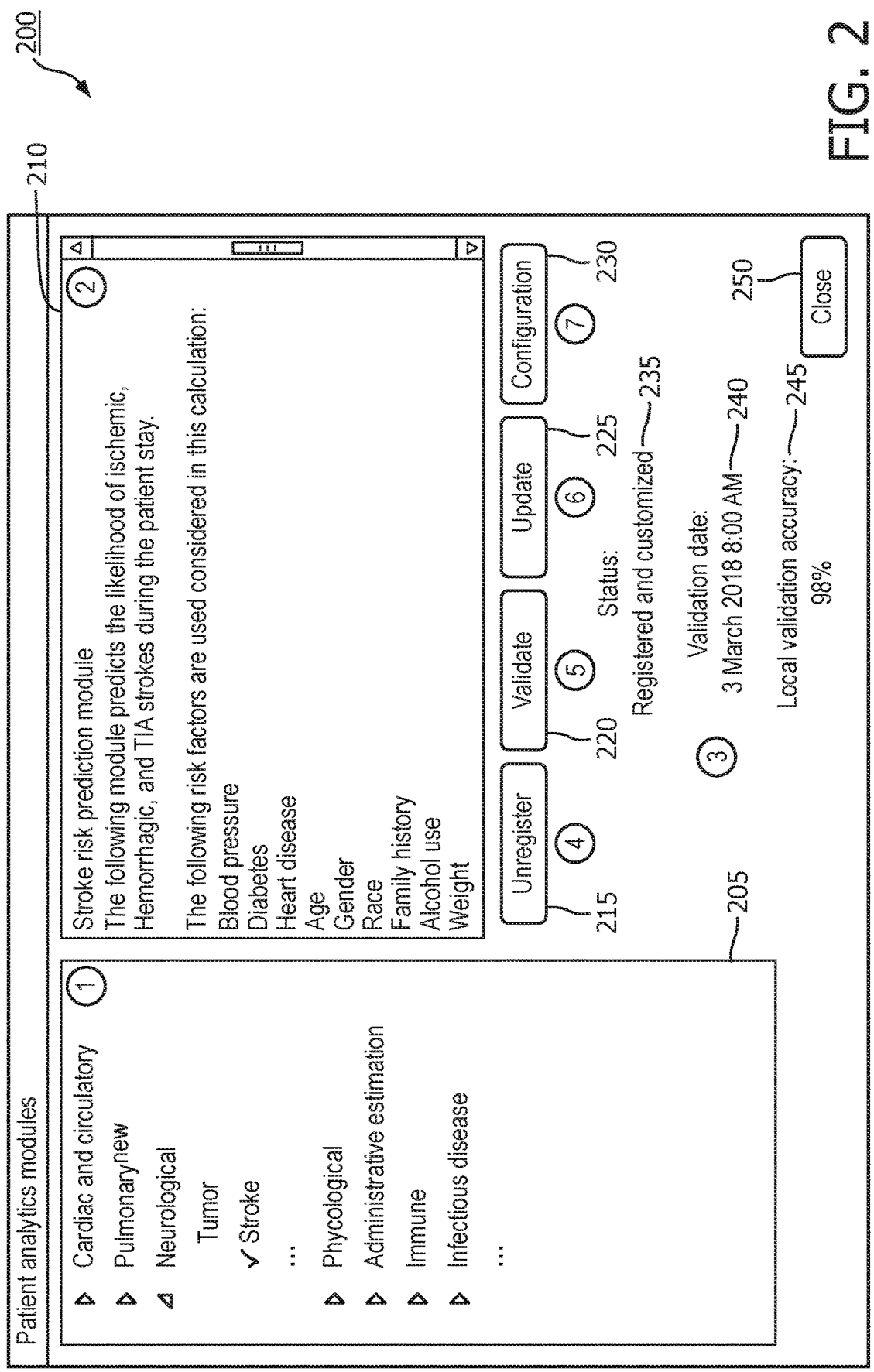
FIG. 2 illustrates a patient analytics modules graphical user interface (GUI) 200 used by a clinician to configure the machine learning models.

Now an example workflow using the modular patient analytics system 100 will now be provided to further describe the modular patient analytics system 100. First, the setup of the modular patient analytics system 100 will be described including model configuration and mapping of the EMR data elements to coding systems such as SNOMED and LOINC. FIG. 2 illustrates a patient analytics modules graphical user interface (GUI) 200 used by a clinician to configure the machine learning models. The patient analytics modules GUI 200 includes a list 205 of available analytic machine learning modules, grouped by the medical conditions and body systems, which may be integrated, removed, or further configured for use in the patient analytics system 100. A machine learning module description pane 210 displays a detailed description of the selected machine learning module including all medical information used in the prediction process, the model outputs, the expected use cases for the module, etc. The integration status of the selected module is shown including if and when it was registered and customized 235, the date of the latest validation date 240, and the validation accuracy against the local EMR data 245.

The user is given the option to unregister the current selected analytics module 215. For a module that has not yet been registered, this button 215 will have the text "Register" and will bring the user to module configuration, customization, and validation. Further, the user has the option to re-validate 220 the currently registered modules against a database to confirm the current model still accurately depicts their current patient data. Also, the user may update 225 (re-train) the machine learning model of the current selected module and registered module to account for new patient data. This will lead the user back down the configuration, customization, and validation workflow. Finally, the user may change the configuration of the currently selected and registered module and remap inputs and outputs of the underlying models 230. Once the user has completed the configuration of the machine learning models, the close button 250 may be used to exit the configuration.

Figure 3:
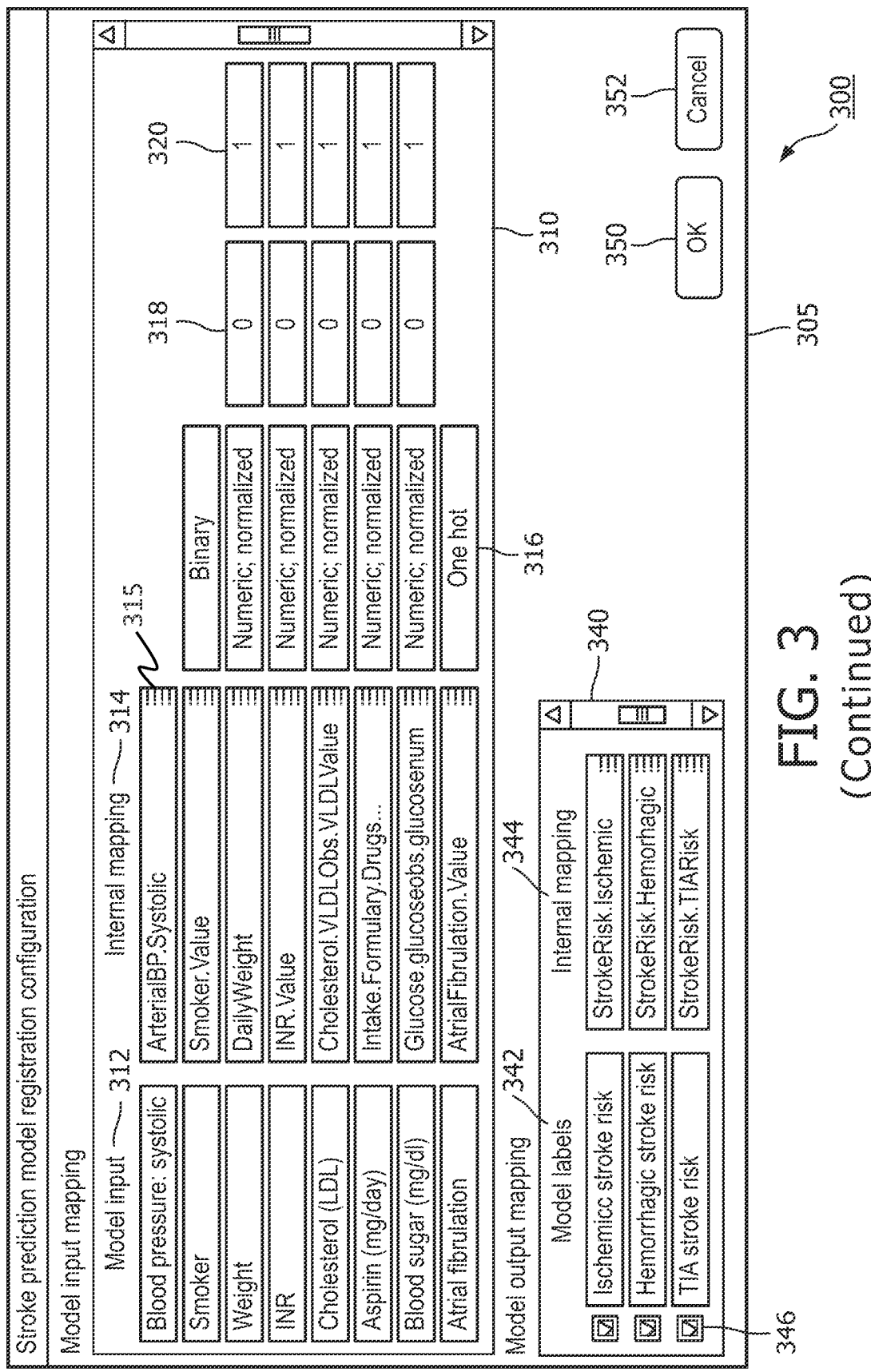
FIG. 3 illustrates a machine learning model registration configuration GUI for setting up the model configuration and mapping EMR data elements to coding systems.

FIG. 3 illustrates a machine learning model registration configuration GUI for setting up the model configuration and mapping EMR data elements to coding systems (e.g., SNOMED, LOINC). A user sets the model input mapping by first specifying the EMR data elements used for model input. The GUI 300 includes a model pane 305. The model pane 305 further includes a model input mapping pane 310 and a model output mapping pane 340. The user in this example has selected the stroke prediction model as is shown at the top of the model pane 305. The model input mapping pane 310 includes a list of model inputs 312, a list of internal mappings 314 associated with the model inputs, a list of encodings 316, a list of normalization minimums 318, and normalization maximums 320. The user may click on details icon 315 to search for data elements. By default, data elements are selected based the data required for the specific model. Clicking on the details icon 315 opens a search pane 322. The search pane 322 may include a search box 324, a search type box 326, a results pane 328, a SNOMED CT concepts box 330, and a concept details box 332.

The user may select the encoding 316 to be used for the internal data for the module input 312 using the corresponding encoding box. Further, the user may modify the normalization range for numeric input data by setting the corresponding normalization minimum 318 and normalization maximum 320.

The model output mapping pane 340 may include a list of model labels 342 and a corresponding list of internal mappings 344. The user may select which model outputs are stored in the EMR using the check boxes 346 associated with the list of model labels 342. Next, the user may select the model output to internal mappings 344. The user continues by clicking the OK button 350 or abandons the configuration by clicking the cancel button 352. The OK button 350 will continue the registration process to the module validation GUI.

FIG. 4 illustrates the custom training data GUI 400. The custom training data GUI 400 may include boxes for selecting a start date 402 and an end date 404. If the user chooses to customize the model with local data, the user first selects the time range of the local data to include in the customized model using the start data box 402 and the end date box 404.

The user may select to employ automatic filtering of local data to filter out irrelevant and anomalous data by checking automatic filtering box 406. Filtering will occur based off specifications defined internally in the analytics module.

The custom training data GUI 400 may further include a sample data pane 420 that displays all of the available data samples to train the model. The sample data pane 420 includes use sample check boxes 422 that indicate that a specific sample is to be selected for inclusion in the training data. The sample data pane 420 may display the sample ID 424, patient ID 426, admission date 428, discharge date 430, and multiple fields of relevant clinical data for the current selected module for the various data samples. It is noted that other data values for the data samples may be displayed as well depending on the model selected or other requirements. Further, there may be multiples samples for the same patient at different times during their stay.

The user may individually select or unselect samples to be used in module training. For a given sample, all module inputs may be displayed in anonymized form. The select all box 414 or unselected all box 416 may be used to select all data samples or unselect all data samples.

The user may save the current training data (both selected and unselected) locally using the save as box 408. This may be necessary if the user decides to individually inspect training samples. The user has the ability to import previously saved training data and configurations using the import box 410 as long as they match the current model configuration. To allow for easier processing, the user is able to open the current training set in Microsoft Excel which is linked with the training data in sample data pane 420 using the open in Excel box 412. Once data has been selected, user may press the OK button 440 to continue to model validation or the cancel button 442 to abandon the model customization.

Figure 5:
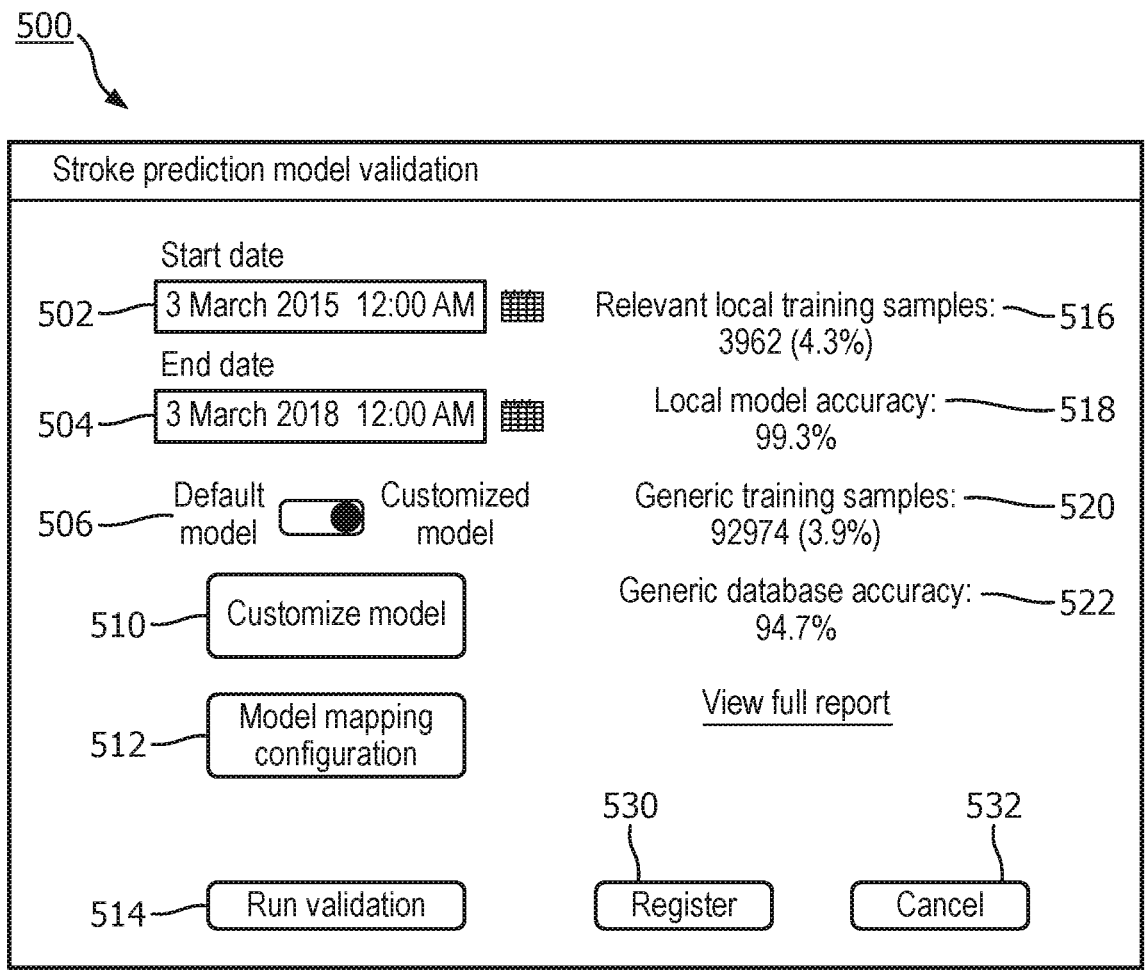
FIG. 5 illustrates a train and validate GUI.

FIG. 5 illustrates a train and validate GUI 500. The train and validate GUI 500 may use site specific data to validate existing models and/or train new models. The user may select the time range of local data samples to validate the models against using the start data box 502 and end data box 504. Next, the user may select whether to use the provided default model or a customized version of the models trained with local patient data using the model selector 506. The user may further customize the model by selecting new data samples using the customize model button 510 or updating the module to EMR mapping using the model mapping configuration button 512 if they are unhappy with the results. The user may validate the module using the run validation button 514. If the customized model is selected and the module has not yet been trained with the current module local training data, anonymized local data will be uploaded, and a customized model will be trained.

After the customized model is trained or if the user selects to use the default model, the model is run against the local training sample and module server samples to determine the overall model accuracy. The results may be displayed to the user as shown with a detailed report available to better analyze any point of failure for the model. The results display includes the number of relevant local training samples 516, the local model accuracy 518, the number of generic training samples 520, and the generic database accuracy 522. The OK button (not shown) becomes a register button 530 if the user has made any changes to the current module. If the user enters the validation dialog from the module selection dialog for an already registered module, running validation to confirm that the module is still valid with the latest EMR data will not change the current module and the register button 530 will appear as an OK button. The last validation results will be saved when the user presses the OK (Register) 530 button. The user may also cancel the operation by pressing the cancel button 532.

Figure 6:
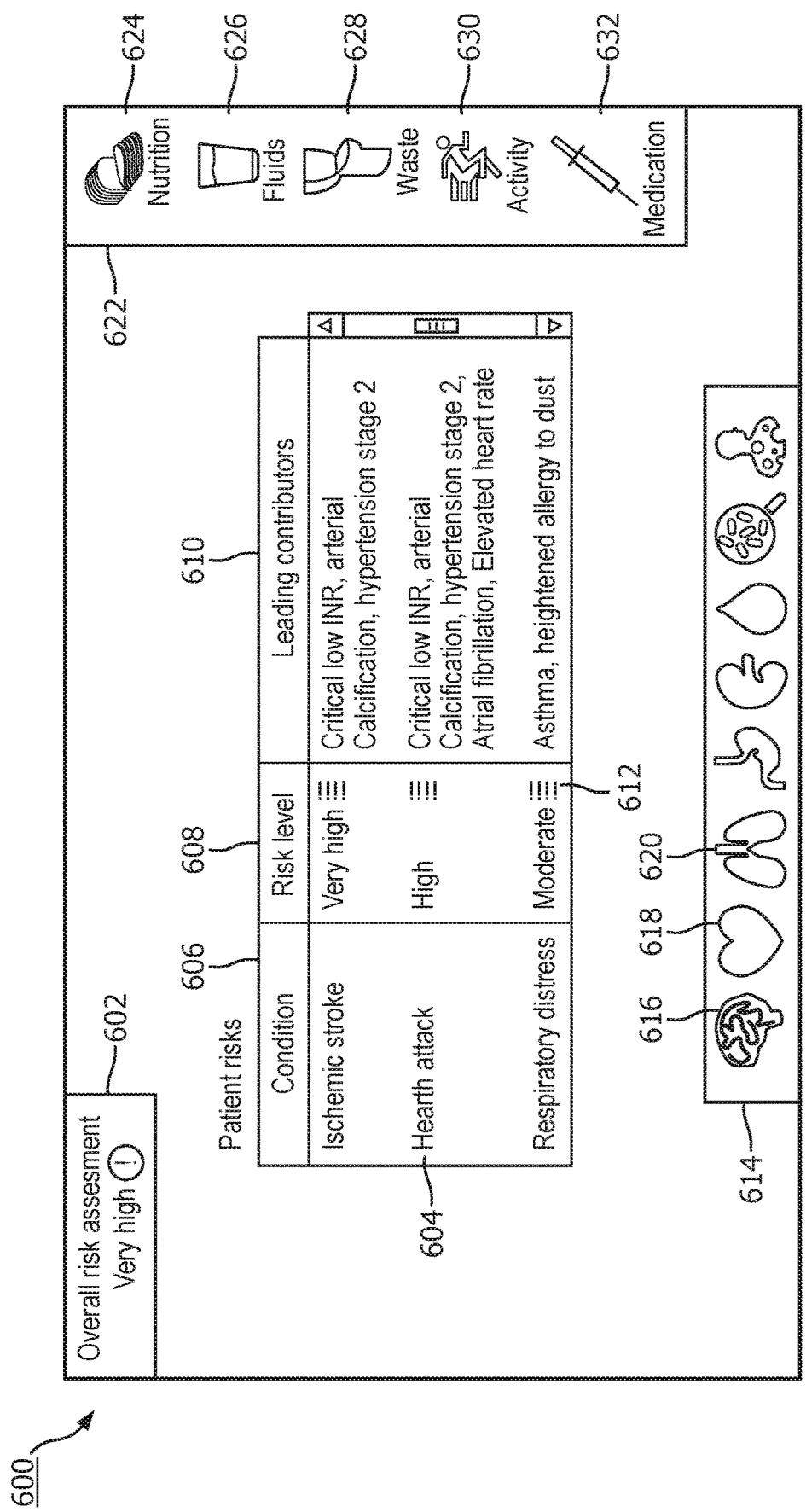
FIG. 6 illustrates a customizable dashboard.

FIG. 6 illustrates a customizable dashboard. The customizable dashboard 600 may be an overall risk GUI. The customizable dashboard 600 may integrate into existing EMRs. The overall patient risk is determined by all registered analytic modules from the severity of the predicted conditions and the risk level of the patient developing the listed conditions, and the overall patient risk is displayed 602 on the customizable dashboard 600. A major body system pane 614 includes icons for major body systems such as for example the brain 616, the heart 620, the lungs 620, etc. The overall risk pertaining to each major body system may be indicated by the color of the icons for each major body system, such as for example, translucent green for no risks identified, to yellow for moderate risks identified, to red to indicate critically high risks. Each icon may be selected to display a listing the potential conditions leading to this assessment. Further, a patient risks pane 604 lists the different patient risk conditions 606, the associated risk level 608 along with leading contributors 610. A detailed description maybe obtain of how the risk level was calculated and all contributing factors is available by clicking on the details icon 612 in the corresponding risk level cell.

Patient care alerts are displayed in a patient care alerts pane 622. The patient care alerts pane 622 include various icons for different care alerts, for example nutrition 624, fluids 626, waste 628, activity 630, and medication 632. Patient care alerts are determined from charted goals, orders, and patient intake and are available as part of risk mitigation and as a scheduling assistant for nutrition 624, fluids 626, waste 628, activity 630, and medication 632 events. The patient care icons may have on and off states. The patient care icons display the related orders, requirements, and goals when the associated icon is selected, and the state of patient care icons changes as charted data is received.

The modular patient analytics system provides various technological benefits in solving the technological problem of testing, developing, verifying and deploying various machine learning tools in patient care and assessment. Further, the modular solves the problem of care providers being overloaded with patient information and not being able to quickly and accurately diagnose and treat acute patient conditions because of data overload. The modular patient analytics system may be implemented with any product that uses medical standardized coding systems (such as SNOMED, LOINC) and that could benefit from machine learning capabilities. The modular patient analytics system embodiments describe herein may be integrated into an EMR as a go to dashboard providing clinicians with important indicators and predictions for a variety of patient conditions. EMR integration could also be used to provide an early warning system for many life-threatening patient conditions, directing clinician care to higher risk factors both in a predictive fashion and as reminders, reducing the risk of error and associated liability.

The various GUIs included herein are provided as examples only. The GUIs may include other elements and be in other configurations in order to provide the functionality described.

Alternatively, the modular patient analytics system may be implemented as a standalone application for machine learning model development in healthcare research and applications, cutting the time, resources and expertise needed to develop, validate and integrate useful machine learning models.

The embodiments described herein may be implemented as software running on a processor with an associated memory and storage. The processor may be any hardware device capable of executing instructions stored in memory or storage or otherwise processing data. As such, the processor may include a microprocessor, field programmable gate array (FPGA), application-specific integrated circuit (ASIC), graphics processing units (GPU), specialized neural network processors, cloud computing systems, or other similar devices.

The memory may include various memories such as, for example L1, L2, or L3 cache or system memory. As such, the memory may include static random-access memory (SRAM), dynamic RAM (DRAM), flash memory, read only memory (ROM), or other similar memory devices.

The storage may include one or more machine-readable storage media such as read-only memory (ROM), random-access memory (RAM), magnetic disk storage media, optical storage media, flash-memory devices, or similar storage media. In various embodiments, the storage may store instructions for execution by the processor or data upon with the processor may operate. This software may implement the various embodiments described above.

Further such embodiments may be implemented on multiprocessor computer systems, distributed computer systems, and cloud computing systems. For example, the embodiments may be implemented as software on a server, a specific computer, on a cloud computing, or other computing platform.

Any combination of specific software running on a processor to implement the embodiments of the invention, constitute a specific dedicated machine.

As used herein, the term "non-transitory machine-readable storage medium" will be understood to exclude a transitory propagation signal but to include all forms of volatile and non-volatile memory.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A modular patient analytics system, comprising:
a database comprising site data, the site data comprising patient data and site training data, wherein the patient data comprises one or more types;
an integrated machine learning module configured to: (i) receive the patient data extracted from the site data and (ii) apply one or more machine learning models to the received patient data;
a model training service configured to: (i) receive the site training data extracted from the site data, and (ii) train a first machine learning model using the site training data to generate a first trained machine learning model;
machine learning services that includes the one or more machine learning models comprising: (i) one or more default machine learning models, wherein the one or more default machine learning models are trained using external patient data, other than the site data; and (ii) one or more trained machine learning models, wherein the one or more trained machine learning models comprises the first trained machine learning model;
a patient analytics modules graphical user interface configured to allow a user to select which of the one or more machine learning models to use from the machine learning services, wherein the patient analytics modules graphical user interface is configured to present a list of the one or more machine learning models based upon the one or more types of the patient data in the site data, and is further configured to receive, by the user, the selection of which of the one or more machine learning models to use from the machine learning services; and
a testing service configured to: (i) receive real time patient data from an electronic medical records system, (ii) run, using the received real time patient data, the selected one or more of the one or more default machine learning models or the one or more trained machine learning models from the machine learning services to produce a model output, and (iii) provide the model output to the integrated machine learning module.

2. The modular patient analytics system of claim 1, further comprising a patient data graphical user interface configured to extract the patient data from the site data, and to provide the extracted patient data to the integrated machine learning module.

3. The modular patient analytics system of claim 1, wherein the patient analytics modules graphical user interface is configured to receive an input from the user to validate the selected machine learning model.

4. The modular patient analytics system of claim 1, wherein the patient analytics modules graphical user interface is configured to receive an input from the user to unregister the selected machine learning model.

5. The modular patient analytics system of claim 1, wherein the patient analytics modules graphical user interface is configured to receive an input from the user to update the selected machine learning model.

6. The modular patient analytics system of claim 1, wherein the patient analytics modules graphical user interface is configured to display validation information regarding the selected machine learning model.

7. The modular patient analytics system of claim 6, wherein the validation information includes at least one of validation status, validation date, local validation accuracy, and generic database accuracy.

8. The modular patient analytics system of claim 1, further comprising an overall risk graphical user interface configured to display patient risk information for a selected patient, the risk information determined at least in part by applying one or more of the one or more default machine learning models or the one or more trained machine learning models to patient data of the selected patient.

9. The modular patient analytics system of claim 8, wherein the overall risk graphical user interface further includes a listing of patient risks, an associated risk level, and associated leading contributors.

10. The modular patient analytics system of claim 8, wherein the overall risk graphical user interface further includes a set of icons indicating various body systems of the selected patient, and wherein the appearance of each of the set of icons is varied based upon a risk level for each body system of the selected patient.

11. The modular patient analytics system of claim 8, wherein the overall risk graphical user interface further includes an overall risk assessment of the selected patient.

12. The modular patient analytics system of claim 8, wherein the overall risk graphical user interface further includes a set of icons indicating one or more patient care alerts.

13. The modular patient analytics system of claim 12, wherein the patient care alerts include one or more of nutrition, fluids, waste, activity, and medication.

14. The modular patient analytics system of claim 1, further comprising a machine learning model registration configuration graphical user interface configured to display one or more machine learning model inputs and associated internal mappings, encodings, normalization minimums, and normalization maximums.

15. The modular patient analytics system of claim 14, wherein the machine learning model registration configuration graphical user interface is configured to allow a user to change one or more values for the associated internal mappings, the normalization minimums, and the normalization maximums.

16. The modular patient analytics system of claim 1, further comprising a module custom training graphical user interface configured to display sample patient data and to allow a user to select the site training data to train the first machine learning model.

17. The modular patient analytics system of claim 16, wherein the module custom training graphical user interface is configured to allow the user to select a start date and end date for the sample patient data and to select the sample patient data based upon the selected start date and end date.

18. The modular patient analytics system of claim 17, wherein the module custom training graphical user interface includes a save as icon and an import icon, and wherein the selected sample patient data is saved when the user selects the save as icon and the selected sample patient data is imported from an external source when the user selects the import icon.

19. The modular patient analytics system of claim 1, further comprising a classification service configured to: (i) receive the patient data extracted from the site data and (ii) run one or more of the one or more machine learning models on the received patient data to validate a second machine learning model.

20. The modular patient analytics system of claim 1, further comprising a classification service configured to: (i) receive vetted data and (ii) run the first trained machine learning model on the received vetted data in order to attempt to validate the first trained machine learning model.

21. A method using a modular patient analytics system, the method comprising:
 receiving, by an integrated machine learning module of the modular patient analytics system, patient data extracted from site data stored in a site data database;
 applying, by the integrated machine learning module, one or more machine learning models to the received patient data;
 receiving, by a model training service of the modular patient analytics system, site training data extracted from the site data to train a first machine learning model;
 training, by the model training service using the received site training data, a first machine learning model to generate a first training machine learning model;
 providing, by machine learning services of the modular patient analytics system, one or more default machine learning models and one or more trained machine learning models, wherein the one or more trained machine learning models comprises the first trained machine learning model, and wherein the one or more default machine learning models are trained using external patient data other than the site data;
 receiving, via a patient analytics modules graphical user interface, a selection of which of the one or more machine learning models to use from the machine learning services, wherein the patient analytics modules graphical user interface is configured to present a list of the one or more machine learning models based upon the one or more types of the patient data in the site data;
 receiving, by a testing service of the modular patient analytics system, real time patient data from an electronic medical records system;
 running, using the received real time patient data, the selected one or more of the one or more default machine learning models or the one or more trained machine learning models from the machine learning services to produce a model output; and providing the model output to the integrated machine learning module.

22. The method of claim 21, further comprising extracting, by a patient data graphical user interface of the modular patient analytics system, the patient data from the site data, and providing the extracted patient data to the integrated machine learning module.

23. The method of claim 21, further comprising displaying, by a machine learning model registration configuration graphical user interface of the modular patient analytics system, one or more machine learning model inputs and associated internal mappings, encodings, normalization minimums, and normalization maximums.

24. The method of claim 21, further comprising:
receiving, by a classification service of the modular patient analytics system, the patient data extracted from the site data; and
running one or more of the one or more machine learning models on the received patient data to validate a second machine learning model.

25. The method of claim 21, further comprising:
receiving, by a classification service of the modular patient analytics system, vetted data; and
running the first trained machine learning model on the received vetted data.

* * * * *